United States Patent [19]
Jacobsen et al.

[11] Patent Number: 6,045,534
[45] Date of Patent: Apr. 4, 2000

[54] DISPOSABLE FLUID INJECTION MODULE

[75] Inventors: Stephen C. Jacobsen; Aaron M. Best; Tomasz J. Petelenz; M. Mary Sinnott, all of Salt Lake City, Utah

[73] Assignee: Sarcos, Inc., Salt Lake City, Utah

[21] Appl. No.: 08/957,520

[22] Filed: Oct. 27, 1997

Related U.S. Application Data

[63] Continuation-in-part of application No. 08/797,295, Feb. 7, 1997, Pat. No. 5,860,957.

[51] Int. Cl.[7] .................................................. A61M 65/02
[52] U.S. Cl. .............................. 604/156; 604/30; 604/65; 604/140
[58] Field of Search .................. 604/140, 49, 51, 604/68, 69, 131, 141, 143, 144, 145, 146, 147, 156, 30

[56] References Cited

U.S. PATENT DOCUMENTS

| | | |
|---|---|---|
| 3,840,009 | 10/1974 | Michaels et al. . |
| 3,977,402 | 8/1976 | Pike ................................. 604/144 X |
| 4,102,332 | 7/1978 | Gessman . |
| 4,141,359 | 2/1979 | Jacobsen et al. . |
| 4,250,878 | 2/1981 | Jacobsen et al. . |
| 4,312,347 | 1/1982 | Magoon et al. . |
| 4,326,522 | 4/1982 | Guerrero et al. . |
| 4,425,117 | 1/1984 | Hugemann et al. . |
| 4,439,197 | 3/1984 | Honda et al. . |
| 4,457,752 | 7/1984 | Vadasz . |
| 4,564,363 | 1/1986 | Bagnall et al. . |
| 4,968,297 | 11/1990 | Jacobsen et al. . |
| 5,135,479 | 8/1992 | Sibalis et al. . |
| 5,167,625 | 12/1992 | Jacobsen et al. . |
| 5,196,002 | 3/1993 | Hanover et al. . |
| 5,522,798 | 6/1996 | Johnson et al. . |
| 5,527,288 | 6/1996 | Gross et al. . |
| 5,582,593 | 12/1996 | Hultman . |
| 5,616,132 | 4/1997 | Newman . |

*Primary Examiner*—Corrine McDermott
*Assistant Examiner*—Kent Gring
*Attorney, Agent, or Firm*—Thorpe, North & Western

[57] ABSTRACT

An automated injection module is comprised of a housing, a piston drug capsule disposed within the housing, a piston core including a puncture seal membrane defining a reservoir for holding a drug between the puncture seal membrane and the piston drug capsule, an injection device having at least one sharp end for puncturing the puncture seal upon activation of the device, an end cap on a distal end of the housing, and a pressure source on a proximal end of the housing. The pressure source is preferably a propellant that ignites and forces the piston toward the distal end. Substantially simultaneously, the injection device pierces the puncture seal membrane, the piston core is forced into the piston drug capsule, and the drug is evacuated from the reservoir through the injection device and into a patient.

37 Claims, 7 Drawing Sheets

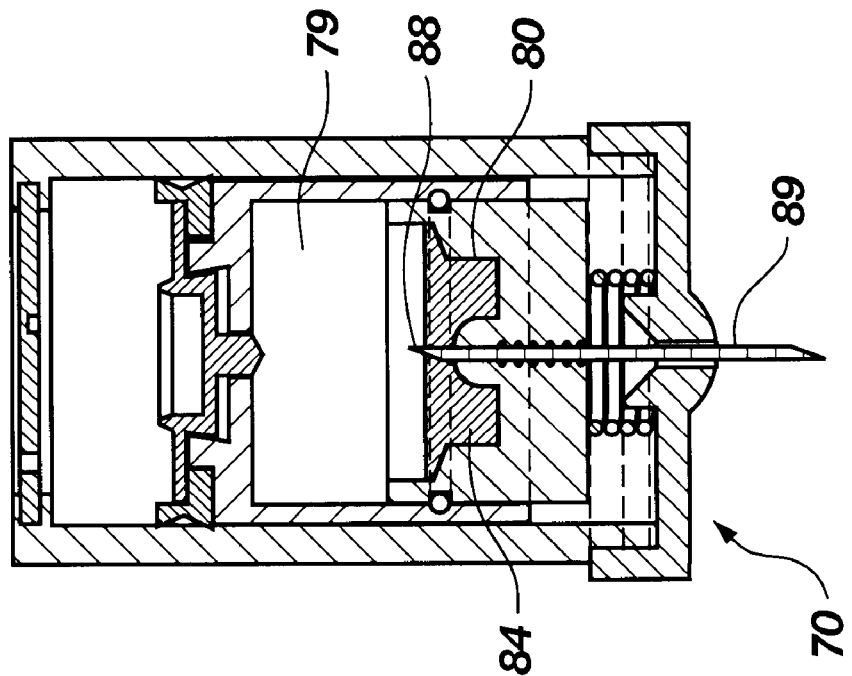
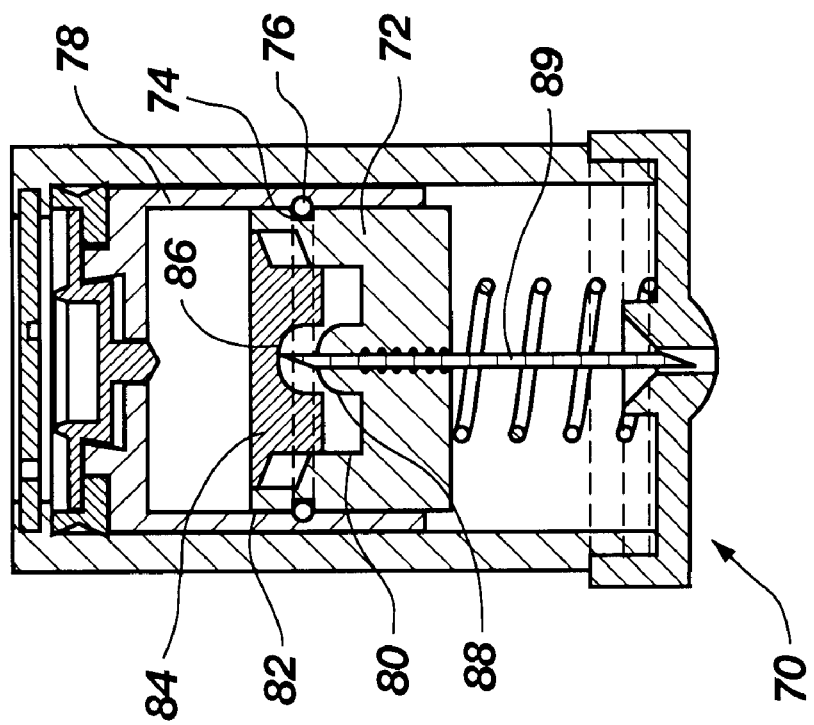
Fig. 3B
Fig. 3A 6,045,534

DISPOSABLE FLUID INJECTION MODULE

This application is a continuation-in-part of U.S. patent application Ser. No. 08/797,295, now U.S. Pat. No. 5,860,957 filed on Feb. 7, 1997.

BACKGROUND

1. Field of the Invention

The present invention relates generally to an apparatus for injecting drugs into a person and, more specifically, to an autoinjection device that utilizes a piston-like assembly and a propellant to automatically inject a single dose of a drug into a person when the propellant is activated.

2. Background of the Invention

Presently available autoinjection systems are relatively large and bulky, requiring skill and training in order to properly operate the device and thus are not amenable to applications for which rapid administration of either a single drug or a combination of different compounds in rapid succession is desirable. Such systems are used mainly for mass vaccinations, self-administration of medications, such as for injection of insulin in diabetic patients, epinephrine in anaphylactic shock, or antimigrain drugs (e.g., sumatriptan). Automated injectors used for mass vaccinations, like in military applications, are typically bulky devices that use the same injection head for all patients and often require an external supply of compressed gas.

Autoinjectors are also presently in use for parenteral administration of medications under field conditions, where injections with a syringe are either impractical or require excessive attention or training. Examples of such situations are administration of chemical warfare antidotes (e.g., atropine) and treatment of anaphylactic shock (e.g., epinephrine). In both instances, drug administration must be rapid, simple and reliable and must minimize the possibility of human error on selection and administration of drug doses. One such autoinjector used by the military comprises an elongate tube with a needle protruding from one end. The needle is rapidly and forcefully inserted into a muscle resulting in the injection of a drug contained within the tube. Upon removal of the needle, however, the needle remains exposed and thus requires proper handling to prevent contact by and injury to other persons.

For mass vaccination programs, reduction of the delivery costs associated with immunizations presents the biggest opportunity to boost immunization coverage rates. One way to decrease costs is to reduce the number of contacts required to complete the immunization series. Frequently, patients' compliance is a major factor limiting effectiveness of mass vaccination programs—children, parents, and health care providers are less willing to accept the increased numbers of separate injections. Thus, it is desirable to deliver as many vaccines as possible during a single, quick patient visit. Mixing of vaccines in one syringe is contraindicated due to reduced potency of the mixed vaccines. However, vaccines are typically safe and effective when administered at the same time at different application sites, such as through a single, multiple-site injection. Therefore, there is a clear need to simultaneously inject several vaccines. Due to problems associated with typical needle injections including transmission of disease between patients, hazards to health-care workers, and expensive handling and disposal procedures, a method of injection without the use of a needle or with a retractable needle is desirable.

U.S. Pat. No. 5,167,625 to Jacobsen et al. discloses an implantable drug delivery system which includes a housing having a plurality of compartments each of which includes a flexible drug containment sack. A cover is disposed over the compartment openings to prevent the release of drug formulation contained in the sacks. Gas generating elements are disposed in the compartments and are responsive to an initiation signal for producing gas to force the sacks and drug formulations out of the housing.

A portable, hand-held injection device is disclosed in U.S. Pat. No. 5,616,132 to Newman and includes a diaphragm mounted within a housing having a needle associated therewith that moves in response to movement of the diaphragm when pressurized gas is released into the housing. Each device, however, is a completely self contained unit that would be relatively expensive to manufacture and difficult, if not impossible, to reuse. Accordingly, such a device would be impractical for mass injection scenarios as previously discussed.

Thus, it would be advantageous to provide a prefilled, interchangeable injection module that is disposable, inexpensive, easy to use, and safe for both the patient and medical personnel. It would also be advantageous to provide a prefilled, interchangeable injection module that reduces risks associated with cross-infection, improves compliance, especially in children, improves the effectiveness of vaccination programs, does not require special sharps handling and has smaller numbers of contaminated items to dispose.

SUMMARY OF THE INVENTION

It is an object of the present invention to provide an autoinjection device that eliminates the need for handling and specialized disposal of contaminated needles.

It is another object of the present invention to provide an autoinjection device that is disposable.

It is yet another object of the present invention to provide an autoinjection device that is easy to use by a person without medical training and minimizes human error associated with the administration of drugs.

It is an object of the present invention to provide an autoinjection device that quickly administers the drug.

It is an object of the present invention to provide an autoinjection device that is compact.

It is an object of the present invention to provide an autoinjection device that is simple to manufacture.

It is an object of the present invention to provide an autoinjection device that reliably delivers a substantially precise dose of a drug.

Accordingly, an apparatus for administering a single dose of a drug in liquid form comprises an outer housing having a proximal end, a distal end, and a first chamber therein that houses a piston drug capsule defining a second chamber. A plunger or piston core fits within the second chamber and defines a reservoir thereinbetween. A drug to be administered is disposed within the reservoir. An injection device such as a needle or nozzle is placed in communication with the reservoir and allows the drug in the reservoir to be injected into a patient. A pressure source in communication with the first chamber is employed to force the piston toward the distal end of the housing. As the piston reaches the distal end, the piston core is forced into the piston, thus forcing the drug out of the reservoir, through the injection device, and into the patient.

Preferably, the piston core includes a puncture seal that provides a seal between the piston core and the piston and maintains the drug in the reservoir until the puncture seal is pierced. The injection device comprises a hollow needle having a sharp end proximate the puncture seal. In operation, as the piston moves toward the distal end of the housing, a first end of the needle exits the housing and enters the skin of a patient. As the piston core moves into the reservoir, a second end of the needle pierces through the puncture seal to allow the drug contained in the reservoir to flow through the needle. A biasing device, such as a coil spring, is preferably provided between an abutment surface or end cap of the injection device and the piston core to retract the needle after delivery of the drug into the patient.

The injection device may also preferably comprise a nozzle in communication with the reservoir such that compression of the plunger into the reservoir forces the drug through the nozzle at such a pressure that the drug is forced through the skin of a patient without insertion of a needle into the patient.

The pressure source preferably comprises a highly combustible material, such as a propellant, that forms a gas when ignited, and an igniter to ignite the combustible material. The igniter is preferably a circuit that utilizes an electrical source, such as a battery, to heat a fusible link, such as a resistor, a screen printed resistor screen printed onto a circuit board, NiCr wire, or tungsten wire, to a temperature at which the propellant ignites and activates the device. A via valve or vent is also preferably provided in the device so that gas generated by the combustion of propellant can be vented to allow the piston and piston core to retract back into the housing. Such a via valve may be filled with a meltable material, such as solder, that can be opened after the drug has been injected to vent the device and allow the needle, if any, to retract back into the device.

BRIEF DESCRIPTION OF THE DRAWINGS

FIGS. 3A and 3B are cross-sectional side views of a partial firing sequence of a second embodiment of an autoinjection module in accordance with the present invention;

DETAILED DESCRIPTION OF THE ILLUSTRATED EMBODIMENTS OF THE INVENTION

Figure 1:
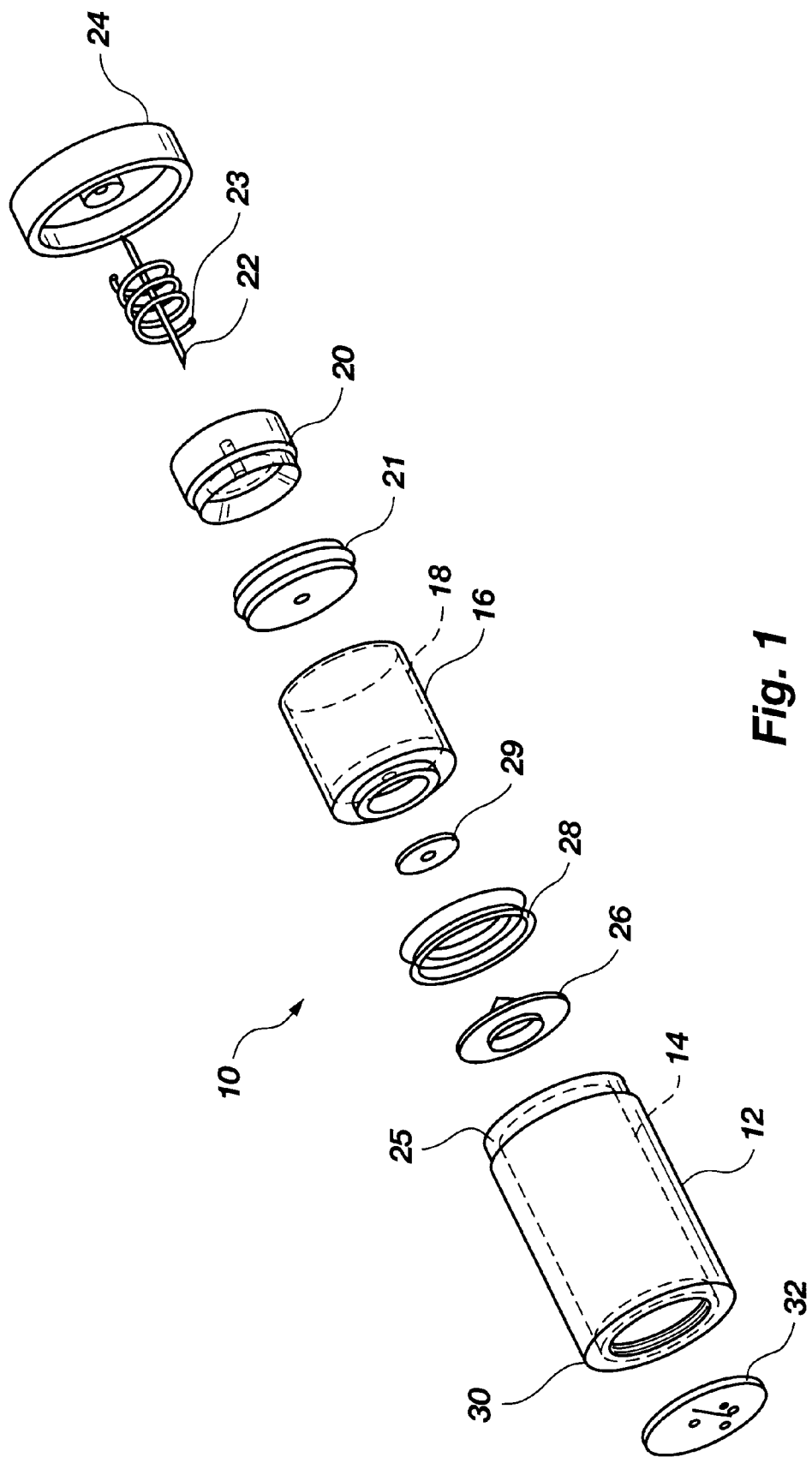
FIG. 1 is an exploded perspective view of a first preferred embodiment of an autoinjection module in accordance with the present invention.

FIG. 1 illustrates an exploded perspective view of an autoinjection module, generally indicated at 10, according to the present invention comprising a housing 12 of generally cylindrical configuration, preferably formed from polycarbonate or other materials known in the art, and defining an interior chamber 14. The rest of the components of the autoinjection module 10 are generally fitted within the chamber 14 or to the housing 12 and include a piston 16 of generally cylindrical configuration, preferably comprised of polycarbonate, that defines an interior chamber or drug capsule 18. A piston core or plunger 20, also preferably comprised of polycarbonate, fits within the drug capsule 18, is provided with a puncture seal or membrane 21, preferably formed from Santoprene or other rubber-like materials known in the art, and forms a reservoir thereinbetween for holding a drug to be administered. An injection device 22, such as a needle formed from a stainless steel or other materials known in the art, is provided in the plunger 20. An end cap 24 that is attachable to the distal end 25 of the housing 12 holds all of the components in the housing 12. A coil spring 23 is provided between the end cap 24 and the piston core 20 in order to bias the piston core 20 and thus the needle 22 away from the end cap 24. The autoinjection module 10 also includes a piston cap 26 for preferably holding a propellant, a piston seal 28 for sealing the piston 16 to the housing 12, and a cap seal 29, preferably comprised of silicone, for sealing the piston cap 26 to the piston 16. The piston cap 26, piston seal 28, and cap seal 29 are each positioned between the proximal end 30 of the housing 12 and the piston 16 in that order. An igniter circuit board 32 is preferably molded into the proximal end 30 of the housing 12 so that it will not become disassociated from the housing 30 when the propellant is ignited and is configured to ignite the propellant upon activation by the igniter circuit board 32.

Figures 2A, 2B, 2C, 2D:
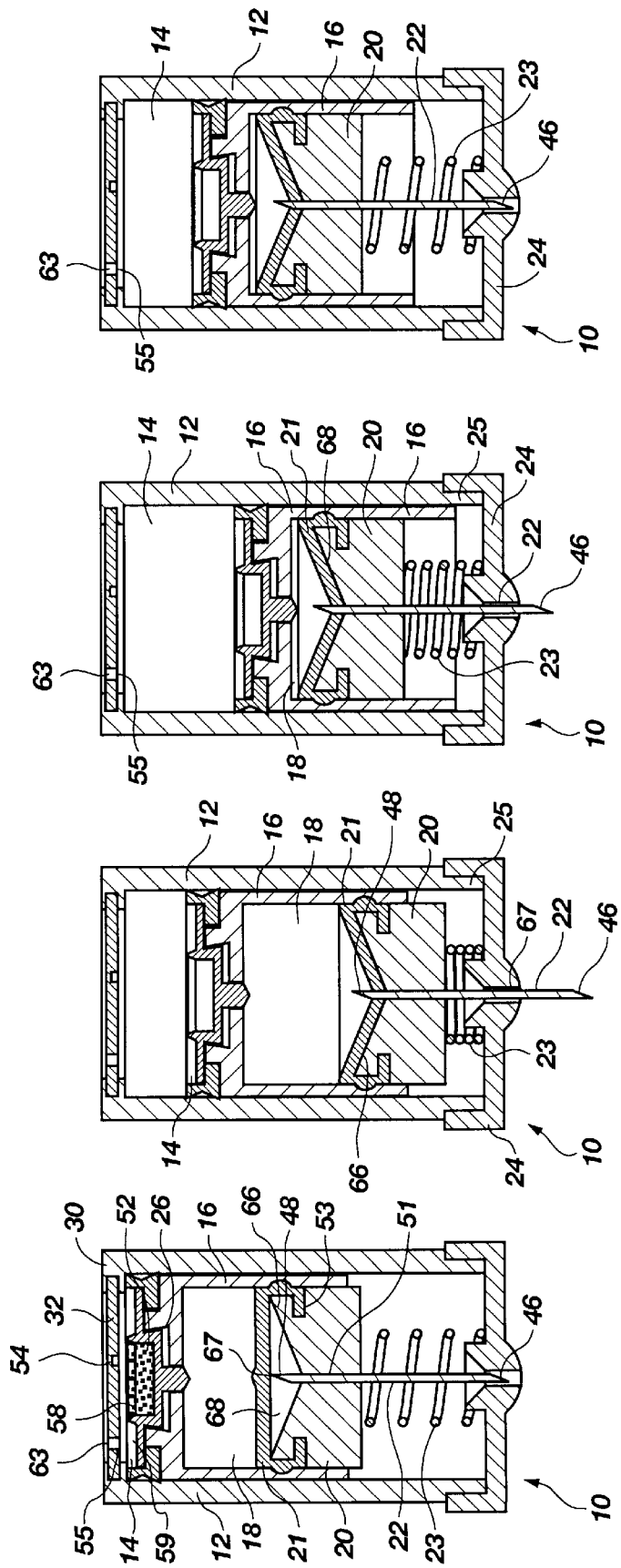
FIGS. 2A, 2B, 2C, and 2D are cross-sectional side views of a firing sequence of the autoinjection module illustrated in FIG. 1.

FIGS. 2A–2D illustrate a firing sequence of the autoinjection module 10 illustrated in FIG. 1 when fully assembled. FIG. 2A shows the autoinjection module 10 in an unused state wherein a drug is disposed within the reservoir or drug capsule 18 and is ready for being dispensed through the injection device 22, in this case a hollow needle having two sharp ends 46 and 48. The piston core 20 securely retains the needle 22 within a longitudinally extending bore 51, as with an adhesive or by tolerance fit, and includes an annular recess or groove 53 formed in its outer surface for retaining the puncture seal 21. In this embodiment, the puncture seal 21 has a disk-like configuration with a "C" shaped cross-section and fits over the proximal end 66 of the piston core 20. The puncture seal 21 thus seals a drug between the drug capsule 18 of the piston 16 and the piston core 20. The puncture seal 21 also includes a recess 67 in its inner surface for receiving and thus aligning the end 48 of the needle 22 when the module 10 is activated. If desired, the puncture seal 21 may have a thinner crosssection at the recess 67 to allow the needle 22 to more easily pierce the puncture seal 21. The distal end 66 of the piston core 20 defines an inwardly tapered frustoconical surface 68 with the end 48 of the needle 22 extending therefrom.

The detonation device or igniter circuit board 32 is secured to the proximal end 30 of the housing 12 to withstand the pressure generated by combustion of the propellant. The igniter circuit 32 is preferably comprised of circuitry capable of igniting a propellant 58, such as smokeless powder, a tetrazine-based compound, or other similar materials known in the art, contained within the recess 52 formed in the piston cap 26. Preferably, the recess 52 is sized to hold a measured amount of propellant 58 such that the desired pressurization of the module 10 is achieved upon ignition of the propellant 58. The printed circuit board 32 is preferably molded into the proximal end 30 of the housing 12, includes at least one fusible link, such as resistor 54, preferably a 1 to 10 ohm 0402 surface mount chip resistor, a screen-printed resistor, a NiCr wire, or tungsten wire, mounted or screened on the back side 59 of the printed circuit board 32 and in contact with or proximate to the propellant 58. At ignition, a power source, such as a 1 to 6 volt battery source, provides current to the resistor 54 and heats it for a relatively short period of time (e.g., 500 ms) to a temperature (e.g., 600 to 700 degrees F) above the ignition point of the propellant 58 (typically about 300 degrees F) and ignites the propellant 58. Upon ignition, the propellant 58 changes from a solid state to a gas state, expands into the chamber 14 defined by the housing 12, and forces the piston 16 away from the proximal end 30 of the housing 12. Depending on the quantity of propellant 58 used, the force on the piston 16 can be controlled. For smokeless powder, about 8 mg of propellant 58 is sufficient to operate the autoinjection module 10. It may be desirable, in order to allow relatively quick retraction of the injection device or needle 22, to provide one or more vents 63 in the printed circuit board 32 filled with a meltable material such as solder or a plastic. Preferably, after ignition, circuitry associated with another resistor 55 is activated and heats the resistor 55 for a period of time (e.g., 0.5 seconds) to melt the solder contained within the via vent 63. When the solder melts, the pressure generated within the chamber 14 forces the melted solder from the via vent 63 and allows the gases generated by ignition of the propellant 58 to escape therethrough. The coil spring 23 can then retract the piston 16 and thus the needle 22 back into the housing 12. It may also be desirable to provide a vent in the housing 12 that allows gases to be vented when the piston 16 has traveled a substantial length of the housing 12.

As further illustrated in FIG. 2B, while the piston 16 travels through the chamber 14 toward the distal end 25 of the housing 12, the plunger or piston core 20 substantially compresses the coil spring 23 until liquid pressure within the drug capsule 18 forces the puncture seal 21 onto and over the end 48 of the needle 22. The piston core 20 then begins to move relative to the piston 16 as coil spring 23 compresses between the end cap 24 and the piston core 20. At this point, the distal end 46 of the needle 22 protrudes through an opening 67 in the end cap 24 in order to penetrate the skin of a user of the autoinjection module 10.

Referring now to FIG. 2C, when the needle 22 pierces the puncture seal 21 and as the piston 16 continues to travel through the chamber 14 of the housing 12, the piston core 20 reaches a point where either compression of the coil spring 23 or engagement of the piston core 20 with the end cap 24 sufficiently forces the piston core 20 into the drug capsule 18 to begin evacuation of a drug contained in the drug capsule 18 through the needle 22. The end cap 24 provides an abutment surface to stop movement of the piston 16 toward the distal end 25. The drug will thus be almost entirely evacuated from the drug capsule 18 except for the amount held between the puncture seal 21 and the piston 16 in the frustoconical surface 68. This remainder of drug can be calculated in order to determine the actual dose of drug that will be administered.

As shown in FIGS. 2C and 2D, the solder contained within the via vent 63 has been melted with the resistor 55 to allow gasses generated by ignition of the propellant 58 (FIG. 2A) to escape from the chamber 14 and allow the coil spring 23 to force the piston 16 and piston core 20 back into the housing 12 a sufficient distance to retract the distal end 46 of the needle 22 at least into the end cap 24. Retraction of the needle 22 is important to eliminate the need for sharps disposal of the autoinjection module 10 and to guard against contact with a non-sterile needle by other persons.

FIGS. 3A and 3B illustrate another preferred embodiment of an autoinrjection module 70 in accordance with the present invention. The module 70 is similar to the autoinjection module illustrated in FIGS. 1 and 2A–2D except that the piston core 72 is provided with an annular O-ring groove 74 for receiving an 0-ring 76 in order to seal the piston core 72 to the piston 78 and defines a puncture seal recess 80 in its proximal end 82. A puncture seal 84 defines a semispherical recess 86 therein for receiving the proximal end 88 of the needle 89. As illustrated in FIG. 3B, when the module 70 is activated and sufficient pressure builds within the drug capsule 79, the puncture seal 84 is forced into the puncture seal recess 80, which is sized and shaped to receive the puncture seal 84. As the puncture seal 84 moves into the recess 80, the proximal end 88 of the needle 89 is forced through the puncture seal 84 and into fluid communication with the drug capsule 79 for evacuation of a drug contained therein.

Figure 4:
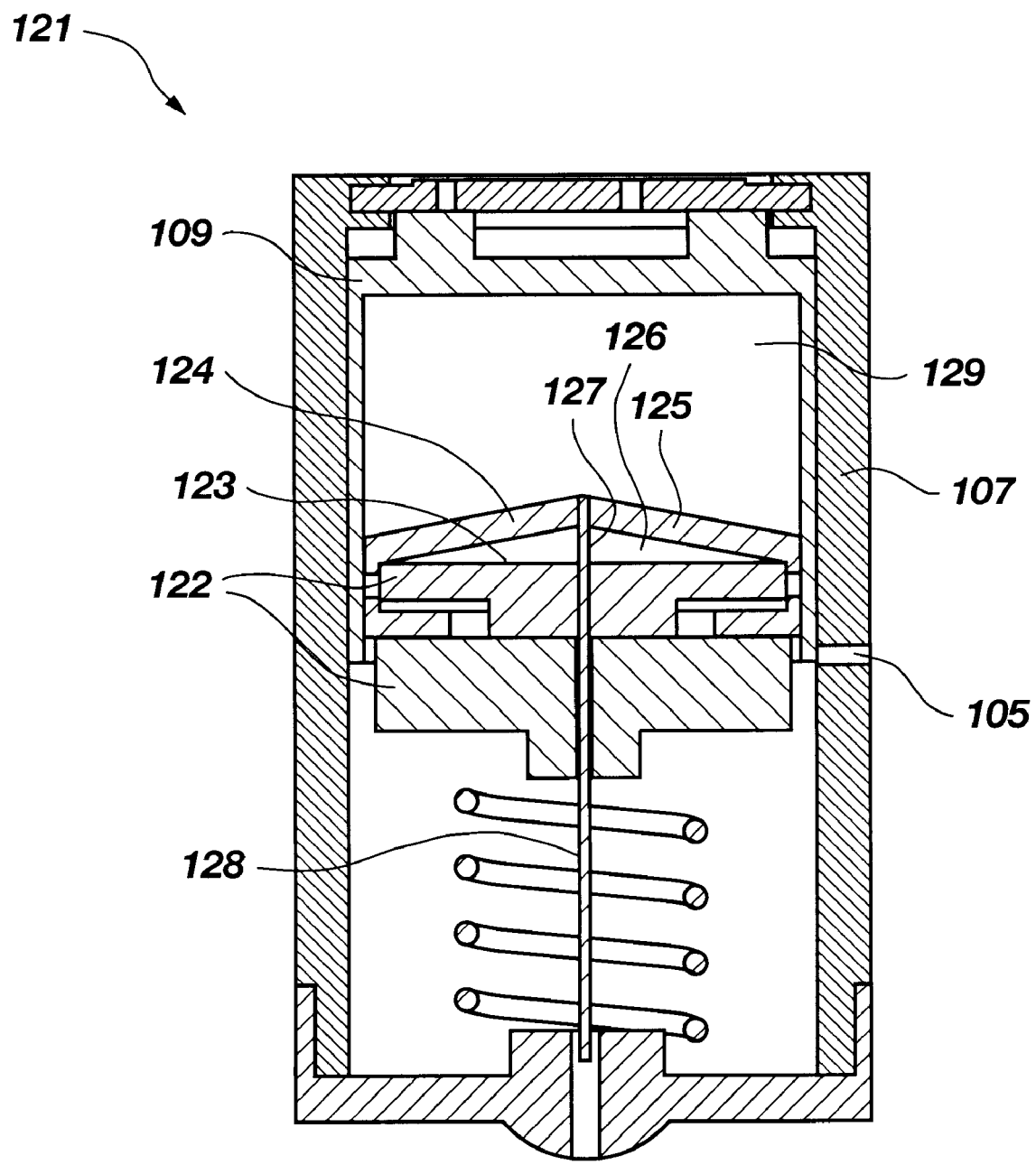
FIG. 4 is a cross-sectional side view of a third embodiment of an autoinjection module in accordance with the present invention.

FIG. 4 illustrates yet another preferred embodiment of an injection module 121 in accordance with the present invention in which a two piece piston core 122 having a relatively planar surface 123 retains a puncture seal 124 having a frustoconical portion 125. The planar surface 123 and frustoconical portion 125 define a space 126 thereinbetween for receiving the proximal end 127 of the needle 128. Thus, as the pressure within the drug capsule 129 becomes sufficiently high, a drug contained therein forces the puncture seal 124 over the proximal end 127 of the needle 128 in order to evacuate the drug. A vent 105 is provided in the housing 107 to vent gas generated during combustion of the propellant once the piston 109 has moved passed the vent 105.

Figure 5:
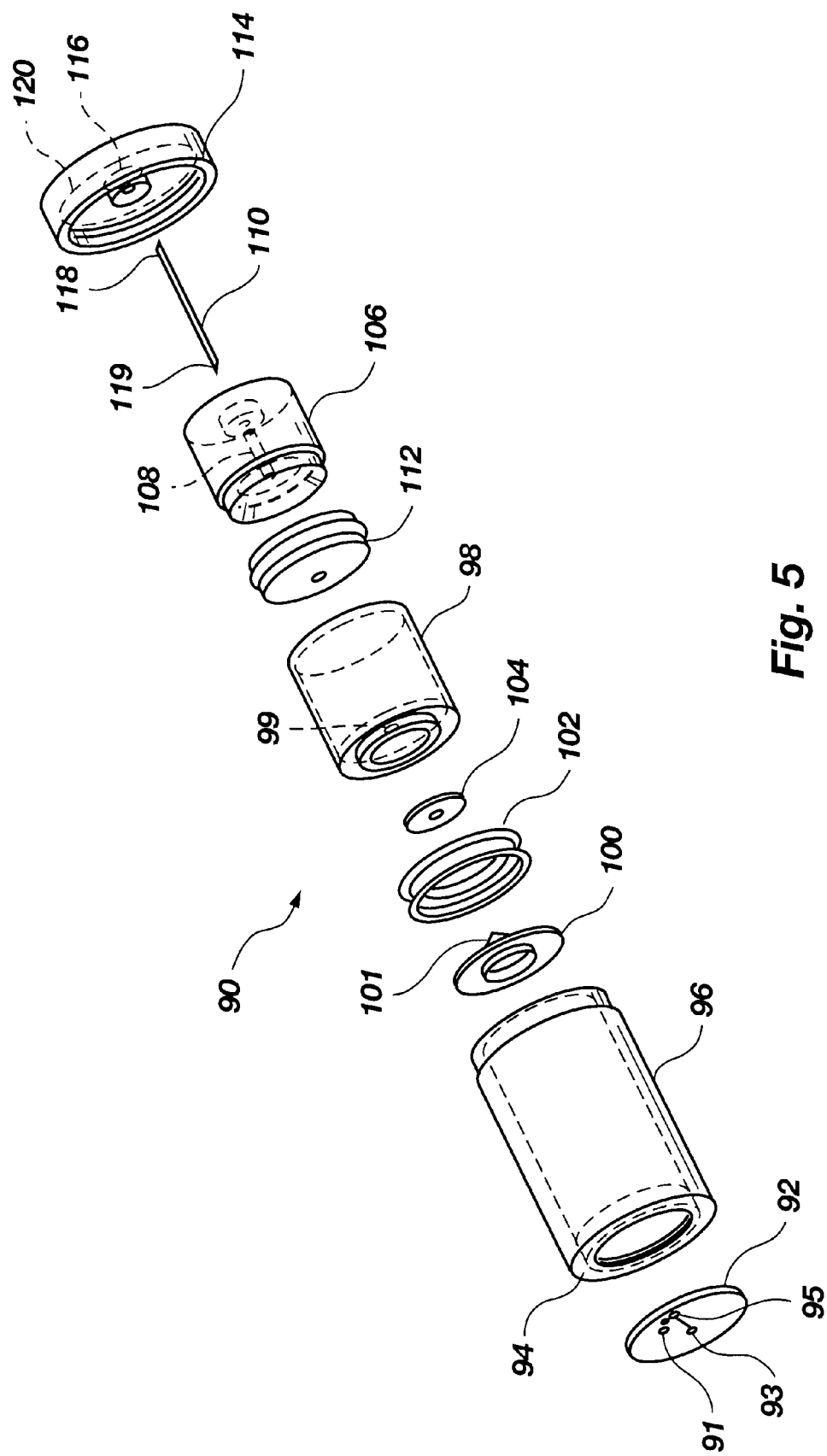
FIG. 5 is an exploded perspective view of a fourth embodiment of an autoinjection module in accordance with the present invention.

Referring to FIG. 5, it is also contemplated that the autoinjection device of the present invention may comprise a needleless or nozzled injection module 90 comprising an igniter circuit 92 attached to the proximal end 94 of the housing 96. A piston drug capsule 98 is sized to fit within the housing 96 and includes a piston cap 100 for holding propellant, piston seal 102, and cap seal 104 to form a substantially air tight seal between the housing 96 and piston drug capsule 98. A nozzle piston core 106 is sized to fit within the piston drug capsule 98 and includes a longitudinally extending bore 108 to secure an elongate nozzle 110 therein. A membrane puncture seal 112 is provided to fit on the nozzle piston core 106 to seal the nozzle piston core 106 to the piston drug capsule 98 and to prevent, until activation of the injection module 90, a drug contained therein from flowing through the nozzle 110. The piston drug capsule 98 may be filled with the drug to be injected through the hole 99 prior to assembly of the module 90. The piston cap 100 includes a protrusion 101 that fits within and seals the hole 99. An end cap 114 that is attachable to the housing 96 includes a bore 116 therethrough into which a distal end 118 of the nozzle 110 can reside upon activation of the module 90.

In this embodiment, the injection module 90 operates in much the same way as the module 10 illustrated in FIGS. 2A–2D, except that the nozzle 110 does not substantially extend beyond the distal end 120 of the end cap 114 upon activation of the device 90 and thus does not penetrate the skin of a person receiving the injection. In addition, the distal end 118 of the nozzle 110 has a blunt end while the proximal end 119 of the nozzle 110 is sharpened to penetrate the membrane puncture seal 112 upon activation of the module 90. Ideally, the distal end 118 extends beyond the distal end 120 of the end cap 114 just enough to make good contact with the skin at the injection site without actually penetrating the skin. Depending on the pressure at which the drug flows through the nozzle 110, however, the nozzle 110 may actually be a distance away from the injection site and still sufficiently administer the drug.

The igniter circuit 92 may include pads 91, 93, and 95 to make electrical contact with a hand-held or other activating device utilizing the injection module 90, similar in nature to the contacts provided in a hand-held flashlight for connection to a battery. If used with some other device, it may be necessary to incorporate alignment features, such as slots or protrusions on the housing 96 and associated protrusions or slots, as the case may be, in the activating device in order to properly align the housing and thus the pads 91, 93, and 95 with their respective contacts provided in the activating device. While the pads 91, 93, and 95 are illustrated as being located at discrete points, the pads may comprise concentric rings such that the module may be at any rotational orientation with respect to an activating device and thus engage their respective electrical contacts independent of rotational orientation. It is also contemplated that an activating device may replace the igniter circuit 92 and provide a spark to the propellant. Likewise, the igniter circuit may include its own power source, such as a battery, so that an external activation device is not required. With such an integral activating device, the housing 96 could be held between the thumb and middle finger and the activating device activated by pressing a button on the igniter circuit 92 with the index finger. Preferably, a non-integral activating device may be removed from the module and reused on other injection modules for subsequent injections.

Figure 6:
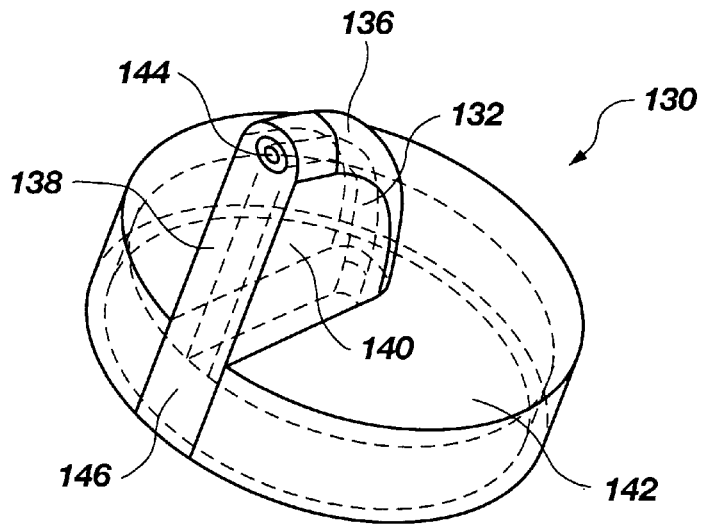
FIG. 6 is a perspective view of an alternative embodiment of an end cap in accordance with the present invention.
Figure 7:
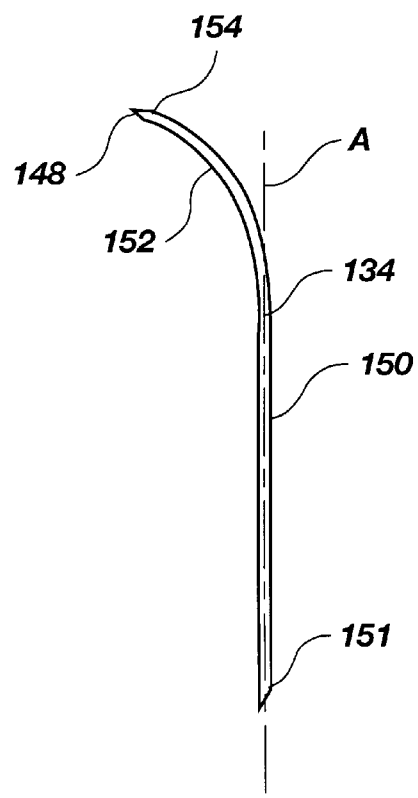
FIG. 7 is a side view of a needle to be used in conjunction with the end cap illustrated in FIG. 6.

As illustrated in FIGS. 6 and 7, the end cap 130 may include a channel 132 therein for encouraging an injection device, in this case needle 134 illustrated in FIG. 7, to bend at some angle relative to the longitudinal axis A of the needle 134. The channel 132 is defined by a curved wall or surface 136 supported by side walls 138 and 140 that depend from the top 142 of the end cap 130. An exit port 144 is defined in the front wall 146 and is aligned with the channel 132 such that as the needle 134 travels through the channel 132, the distal end 148 of the needle 134 will extend through the exit port 144. With such an end cap 130 configuration, an injection module according to the present invention can be placed with the front wall 146 against and substantially parallel to the surface of the injection site.

The needle 134 shown in FIG. 7 will comprise a substantially linear portion 150 having a sharpened end 151, a curved portion 152, and a sharpened tip 154 when inserted into the channel 132 of the end cap 130. Preferably, the needle is comprised of a material used for catheters and the like, such as a nickel/titanium alloy that provides a flexible yet strong needle 134. Accordingly, the needle 135 can bend or deform along the channel 132 as the needle 134 protrudes through the exit port 144. It will be recognized by those skilled in the art, that the needle 134 may be formed from a substantially linear member and that the material from which the needle 134 is formed allows the needle to bend as required.

Figure 8:
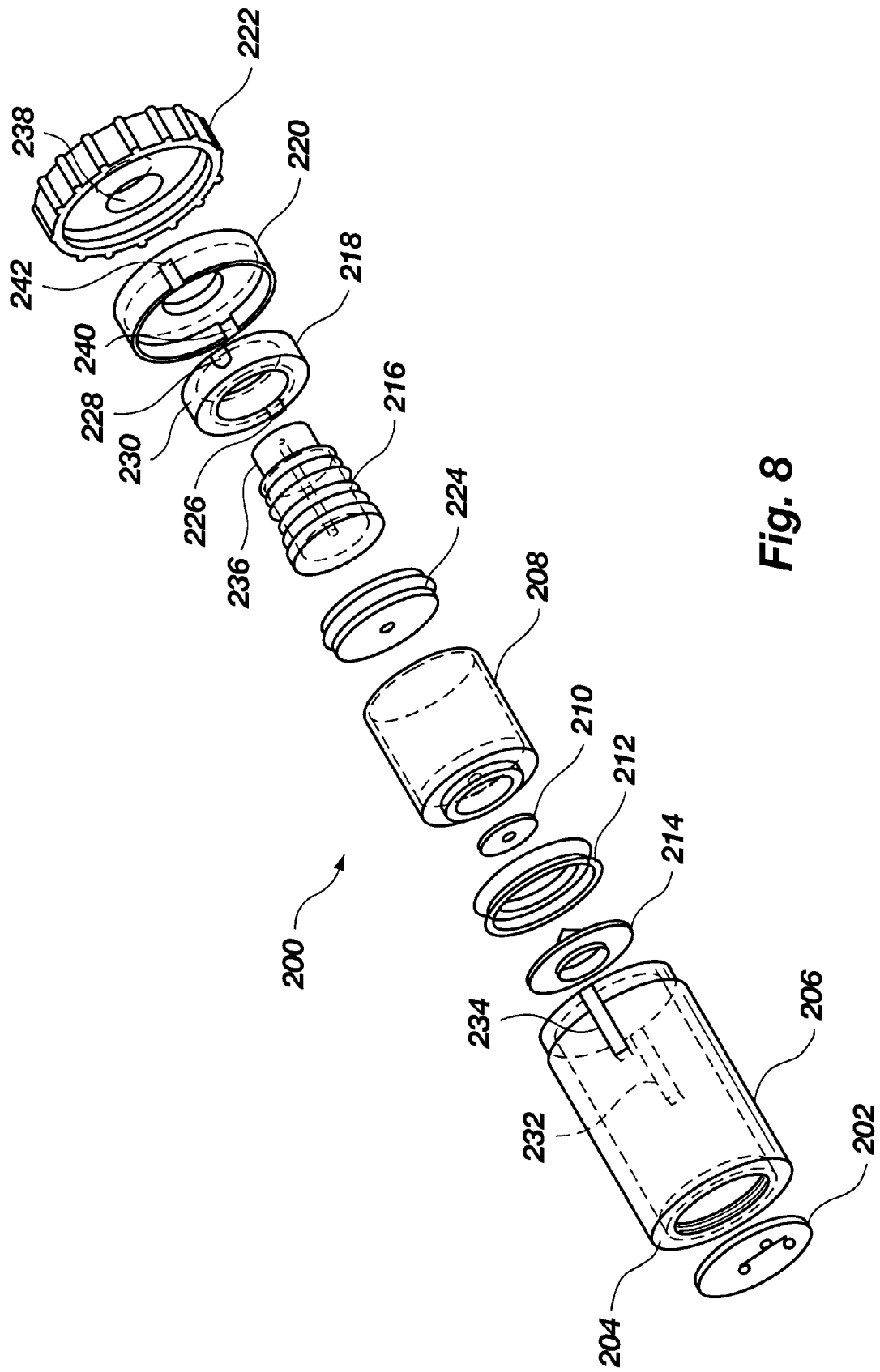
FIG. 8 is an exploded perspective view of a fifth embodiment of an autoinjection module in accordance with the present invention.

In still another preferred embodiment of the present invention, an injection module 200 may be configured to be adjustable such that the volume of the dose of drug to be dispensed may be controlled. As shown in FIG. 8, the adjustable volume injection module 200 comprises a detonation or igniter board 202 secured to the proximal end 204 of a housing 206 and a piston drug capsule 208 including a cap seal 210, a piston seal 212, and a piston cap 214. The module 200 includes an externally threaded spindle 216 to which an internally threaded ring 218 is threadedly engaged. The module 200 also includes an end cap 220, an adjustment knob 222, and a membrane puncture seal 224 that seals the spindle 216 to the piston drug capsule 208.

The threaded ring 218 includes two tabs 226 and 228 laterally extending from the outer surface 230 of the ring 218. The diameter of the ring 218 and the position of the tabs 226 and 228 are configured to engage with and slide within two longitudinally extending slots 232 and 234 defined by the housing 206. When assembled, the smaller distal end 236 of the spindle 216 engages and is secured to the central opening 238 of the knob 222. Thus rotation of the knob 222 causes the spindle 216 to rotate within the housing 206. As the spindle 216 rotates, the ring 218, being held from rotation by the engagement of the tabs 226 and 228 within the slots 232 and 234, respectively, longitudinally moves relative to the spindle 216. The range of movement of the ring 218 and thus the dosage is only limited by the threaded length of the spindle 216 or the lengths of the slots 232 and 234 and thus provides a maximum injectable dose when the ring 218 is abutted against the end cap 220 into slots 240 and 242. When the injection module 200 is activated, the ring 218 provides a stop for the piston drug capsule 208 as it travels through the housing 206. Thus, depending on its position, only a certain quantity of drug will be forced out of the piston drug capsule 208 by the puncture seal membrane 224 and spindle 216 combination. By putting marks indicating dosage on the outside of the housing adjacent the slots 232 or 234 or proximate the knob 222, the position of marks on the tabs 226 or 228 or on the knob 222 relative thereto can indicate the dosage.

It is contemplated that the injection modules herein described may use other propellants to fire the device such as a compressed liquid or gas or other materials known in the art. In addition, the injection modules may be used as individual, self contained units or employed in a single- or multi-injection device that provides a source of electrical current and a handle for gripping by a user. In addition, it is to be understood that the above-described embodiments are only illustrative of the application of the principles of the present invention. Numerous modifications and alternatives may be devised by those skilled in the art, including combinations of the various embodiments, without departing from the spirit and scope of the present invention. For example, the autoinjection modules herein described need not be cylindrical as other configurations such as oval, polygonal, rectangular, and the like may also be possible. In addition, certain features such as the adjustable means could be utilized for both needled and needleless modules. Thus, the appended claims are intended to cover such modifications, alternative arrangements, and combinations.

What is claimed is:

1. An apparatus for delivering a drug, comprising:
    a) a housing disposed within said first chamber, said piston defining a second proximal end and defining a first chamber therein;
    b) a piston disposed within said first chamber, said piston defining a second chamber therein;
    c) a piston core movably disposed within said second chamber of said piston and defining a reservoir between said piston and said piston core;
    d) a pressure source proximate said proximal end and in communication with said first chamber;
    e) an injection device coupled to the piston core and in communication with said reservoir for delivery of a dose of a drug contained therein;
    f) an adjustment device coupled to the housing for adjusting the dose; and
    g) the piston core includes an externally threaded spindle attached on a distal end to an adjustment knob and threadedly engaged with an internally threaded ring, said ring engaged with said housing and providing a stop for said piston upon activation of said pressure source.

2. The apparatus of claim 1, further including a puncture seal coupled to said piston core and interposed between said reservoir and said injection device.

3. The apparatus of claim 2, wherein said puncture seal forms a seal between said piston core and said piston.

4. The apparatus of claim 2, wherein said injection device comprises a hollow needle attached to said piston core and extending toward said distal end.

5. The apparatus of claim 4, wherein said hollow needle is sharp on a first end and a second end, said first end positioned proximate said puncture seal.

6. The apparatus of claim 2, wherein said injection device comprises an elongate nozzle having a sharp end positioned proximate said puncture seal and a blunt end for injecting the drug at an injection site.

7. The apparatus of claim 2, wherein said piston core defines an inwardly tapered frustoconical surface forming a space between said frustoconical surface and said puncture seal and wherein at least a portion of said injection device resides within said space.

8. The apparatus of claim 2, wherein said puncture seal includes a frustoconical portion defining a space between said frustoconical portion and said piston core, and wherein at least a portion of said injection device resides within said space.

9. The apparatus of claim 2, wherein said piston core defines a recess therein sized and shaped to receive said puncture seal therein, said puncture seal positioned proximate said recess and defining a space thereinbetween, and wherein at least a portion of said injection device resides within said space.

10. The apparatus of claim 1, further including a vent in communication with said first chamber.

11. A drug delivery apparatus, comprising:

housing means for providing a first chamber therein;

piston means disposed within said housing means for sliding within said first chamber, said piston means defining a second chamber therein;

plunger means movably disposed within said second chamber of said piston means for forming a reservoir within the piston means;

pressure means for forcing said piston means through said first chamber and said plunger means into said reservoir; and injection means coupled to said plunger means and in communication with said reservoir for delivery of a dose of drug contained within said reservoir.

12. The apparatus of claim 11, further including a sealing means coupled to said plunger means and interposed between said reservoir and said injection means.

13. The apparatus of claim 12, wherein said sealing means forms a seal between said plunger means and said piston means.

14. The apparatus of claim 12, wherein said injection means comprises a hollow needle attached to said plunger means.

15. The apparatus of claim 14, wherein said hollow needle is sharp on a first end and a second end, said first end positioned proximate said sealing means.

16. The apparatus of claim 11, wherein said injection means comprises a nozzle.

17. The apparatus of claim 11, further including venting means for venting said first chamber.

18. The apparatus of claim 17, wherein said venting means further includes disengageable sealing means for allowing ventilation of said first chamber.

19. The apparatus of claim 11, further including adjustment means for adjusting the dose of the drug contained within said reservoir.

20. An apparatus for delivering a drug, comprising:

a) a housing having a first and second chamber therein;

b) a piston, positioned within the housing and between the first and second chambers, having a reservoir therein for containing the drug to be delivered;

c) an injection device, positioned to extend into the reservoir, coupled to the piston and extending into the second chamber, for injecting the drug out of the reservoir; and d) located in the first chamber, a propellant and an electrical circuit that has a first fusible link for igniting the propellant and thereby delivering the drug.

21. The apparatus of claim 20, wherein the electrical circuit is mounted on a printed circuit board that has a vent containing a meltable material and positioned next to a second fusible link.

22. The apparatus of claim 20, wherein the piston further comprises an externally threaded spindle attached on a distal end to an adjustment knob and threadedly engaged with an internally threaded ring that is engaged with the housing and providing a stop for the piston upon activation of the propellant.

23. The apparatus of claim 20, further comprising a biasing device, located in the second chamber, for retracting the injection device after the drug has been delivered.

24. The apparatus of claim 23, wherein the biasing device is a spring positioned around the injection device.

25. The apparatus of claim 20, further comprising an adjustment device coupled to the housing for adjusting a dose of the drug to be delivered.

26. An apparatus for delivering a drug, comprising:

a) a housing having a first and second chamber therein;

b) a piston, positioned within the housing and between the first and second chambers, having a reservoir therein for containing the drug to be delivered;

c) an injection device, positioned to be extended into the reservoir and out of the housing, for delivering the drug out of the reservoir; and d) a biasing device, located proximate the piston, for retracting the injection device into the housing after the drug has been delivered.

27. The apparatus of claim 26, further comprising:

located in the first chamber, a propellant and an electrical circuit including a first fusible link disposed adjacent the propellant for igniting the propellant, which causes the injection device to extend outside the housing to deliver the drug.

28. The apparatus of claim 27, wherein the electrical circuit is mounted on a printed circuit board that has a vent containing a meltable material and positioned next to a second fusible link.

29. The apparatus of claim 26, wherein the piston further comprises an externally threaded spindle attached on a distal end to an adjustment knob and threadedly engaged with an internally threaded ring that is engaged with the housing and providing a stop for the piston upon activation of the propellant.

30. The apparatus of claim 26, wherein the biasing device is a spring positioned around the injection device.

31. An apparatus for delivering a drug, comprising:

a) a housing having a distal end through which the drug is delivered and a proximal end and defining a first chamber therein;
b) a piston disposed within said first chamber, said piston defining a second chamber therein;
c) a piston core movably disposed within said second chamber of said piston and defining a reservoir between said piston and said piston core;
d) a pressure source proximate said proximal end and in communication with said first chamber;
e) an injection device coupled to the piston core and in communication with said reservoir for delivery of a dose of a drug contained therein;
f) a biasing device disposed in the chamber and contacting the piston core for biasing said injection device toward said proximal end;
g) an end cap attached to said distal end of said housing; and
h) the biasing device is a spring interposed between said end cap and said piston core.

32. An apparatus for delivering a drug, comprising:
a) a housing having a distal end through which the drug is delivered and a proximal end and defining a first chamber therein;
b) a piston disposed within said first chamber, said piston defining a second chamber therein;
c) a piston core movably disposed within said second chamber of said piston and defining a reservoir between said piston and said piston core;
d) a pressure source proximate said proximal end and in communication with said first chamber;
e) an injection device coupled to the piston core and in communication with said reservoir for delivery of a dose of a drug contained therein;
f) a biasing device disposed in the chamber and contacting the piston core for biasing said injection device toward said proximal end; and
g) an end cap attached to said distal end of said housing, the end cap includes a curved wall defining a channel therein for encouraging said injection device to bend at an angle relative to a longitudinal axis of said injection device.

33. The apparatus of claim 32, wherein said injection device comprises a hollow needle attached to said piston core and comprised of a nickle/titanium alloy.

34. The apparatus of claim 33, wherein said pressure source is an igniter circuit including at least one resistor and propellant proximate said at least one resistor and said trigger comprises at least one power source for heating said at least one resistor and a switch.

35. The apparatus of claim 34, wherein said at least one resistor is an approximately 1 to 10 ohm resistor and said at least one power source includes at least one battery having a voltage approximately 1 to 6 volts.

36. A drug delivery apparatus, comprising;
a) housing means for providing a first chamber therein;
b) piston means disposed within said housing means for sliding within said first chamber, said piston means defining a second chamber therein;
c) plunger means movably disposed within said second chamber of said piston means for forming a reservoir within the piston means;
d) pressure means for forcing said piston means through said first chamber and said plunger means into said reservoir;
e) injection means coupled to said plunger means and in communication with said reservoir for delivery of a dose of drug contained within said reservoir;
f) the pressure means includes gas generating means for creating a gas and initiating mans for introducing said gas into said first chamber; and
g) the initiating means is an electrical circuit comprising an electrical source and a fusible link, said electrical source providing electrical current to heat said fusible link and ignite said propellant.

37. A drug delivery apparatus, comprising:
a) housing means for providing a first chamber therein;
b) piston means disposed within said housing means for sliding within said first chamber, said piston means defining a second chamber therein;
c) plunger means movably disposed within said second chamber of said piston means for forming a reservoir within the piston means;
d) pressure means for forcing said piston means through said first chamber and said plunger means into said reservoir;
e) injection means coupled to said plunger means and in communication with said reservoir for delivery of a dose of drug contained within said reservoir; and
f) the adjustment means includes adjustable stop means associated with said plunger means for stopping movement of said piston means upon activation of said pressure means.

* * * * *